United States Patent
Siva Kumar et al.

(10) Patent No.: US 10,510,434 B2
(45) Date of Patent: Dec. 17, 2019

(54) DEVICE AND METHOD OF SELECTING PATHWAY OF TARGET COMPOUND

(71) Applicant: Samsung Electronics Co., Ltd, Suwon-si, Gyeonggi-do (KR)

(72) Inventors: Tadi Venkata Siva Kumar, Bangalore (IN); Anirban Bhaduri, Bangalore (IN); Taeyong Kim, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 478 days.

(21) Appl. No.: 15/334,456

(22) Filed: Oct. 26, 2016

(65) Prior Publication Data

US 2017/0235923 A1    Aug. 17, 2017

(30) Foreign Application Priority Data

Feb. 15, 2016 (IN) ............................ 201641005286
May 30, 2016 (KR) ........................ 10-2016-0066358

(51) Int. Cl.
*G16B 5/00* (2019.01)
*G16C 20/10* (2019.01)

(52) U.S. Cl.
CPC ............... *G16B 5/00* (2019.02); *G16C 20/10* (2019.02)

(58) Field of Classification Search
None
See application file for complete search history.

(56) References Cited

U.S. PATENT DOCUMENTS

| | | |
|---|---|---|
| 2003/0220716 A1 | 11/2003 | Mydlowec et al. |
| 2004/0241875 A1 | 12/2004 | Dales et al. |
| 2009/0305364 A1 | 12/2009 | Burgard et al. |
| 2012/0021478 A1 | 1/2012 | Osterhout et al. |

FOREIGN PATENT DOCUMENTS

| | | |
|---|---|---|
| JP | 1999-53425 A | 2/1999 |
| JP | 3689026 B2 | 6/2005 |
| JP | 2008-150337 A | 12/2006 |
| JP | 2011-175454 A | 2/2010 |

OTHER PUBLICATIONS

Moriya, Y., Shigemizu, D., Hattori, M., Tokimatsu, T., Kotera, M., Goto, S., & Kanehisa, M. (2010). PathPred: an enzyme-catalyzed metabolic pathway prediction server. Nucleic acids research, 38(suppl 2), W138-W143. (Year: 2010).*

Oh, M., Yamada, T., Hattori, M., Goto, S., & Kanehisa, M. (2007). Systematic analysis of enzyme-catalyzed reaction patterns and prediction of microbial biodegradation pathways. Journal of chemical information and modeling, 47(4), 1702-1712. (Year: 2007).*

Campodonico et al. "Generation of an atlas for commodity chemical production in *Escherichia coli* and a novel pathway prediction algorithm, GEM-Path," *Metabolic Engineering*, 25, pp. 140-158 (2014).

* cited by examiner

*Primary Examiner* — Bijan Mapar
(74) *Attorney, Agent, or Firm* — Leydig, Voit & Mayer, Ltd.

(57) ABSTRACT

Provided are a method and a device for selecting a pathway for a target compound by combining biochemical and chemical processes together, wherein an input of at least one pathway for synthesis of a target compound or degradation into a target compound is received, hybrid arrangements of one or more reaction steps included in the at least one pathway are predicted, a pathway feasibility score is com-

(Continued)

puted, and at least one hybrid arrangement is selected based on the pathway feasibility score.

20 Claims, 8 Drawing Sheets

BA : Biological Approach; CA: Chemical Approach $f_b(x)$ = function to compute feasibility of biochemical reaction x $f_c(x)$ = function to compute feasibility of chemical reaction x where x is reaction from x1 to x4

$P(f_b)$, $P(f_c)$ represents the power set of feasibility scores of biochemical reactions and chemical reactions, respectively Objective function: $\max(P(f_b), P(f_c))$

DEVICE AND METHOD OF SELECTING PATHWAY OF TARGET COMPOUND

CROSS-REFERENCE TO RELATED APPLICATIONS

This application claims the benefits of Indian Patent Application No. 201641005286, filed on Feb. 15, 2016, in the Indian Intellectual Property Office, and of Korean Patent Application No. 10-2016-0066358, filed on May 30, 2016, in the Korean Intellectual Property Office, the disclosures of which are incorporated herein by reference in their entireties.

BACKGROUND

1. Field

The present disclosure relates to a method and a device for selecting a pathway of a target compound by combining biochemical and chemical processes together.

2. Description of the Related Art

Target molecules are either synthesized or degraded through chemical transformations, and such chemical transformations are the heart of the chemical industry. The chemical transformations require chemical transformations of a target compound through either a chemical approach or a biochemical approach. A chemical or biochemical approach may have both advantages and disadvantages. A process based on a chemical approach (i.e., a chemical process) is easy to scale up and typically exhibits a high kinetic rate. A chemical approach is amicable to greater process conditions. However, a chemical approach often may show poor efficiency for a complex molecule or reactions in multiple steps. In consideration of the number of chemical cross reactions, specificity in chemical transformations may be a challenge. Alternatively, a process based on a biochemical approach (also referred to as a biochemical process) is known to exhibit high synthetic specificity and is able to perform multiple chemical conversions in a single cell without performing an intermediate purification step. A biochemical process also has an additional advantage of being performed under mild conditions. However, the biochemical approach is not as exhaustive as the chemical process. Furthermore, optimal species or microorganisms causing chemical transformations are not easily found.

Therefore, neither a biochemical approach nor a chemical approach provides an efficient and effective strategy for constructing a pathway for transformation of a target molecule.

To design an optimized process, there is a need to consider a hybrid approach by which the biochemical and chemical processes are combined together. However, designing an optimized hybrid approach for processing chemicals is challenging, and experimental designing of such an optimized hybrid approach may not often be feasible.

Therefore, there is a need for a method and a device for selecting effective strategies for chemical and biochemical synthesis/degradation to thereby transform a start compound into a desired target compound through a hybrid approach.

SUMMARY

Provided are a method and a device for selecting a pathway of a target compound.

Additional aspects will be set forth in part in the description which follows and, in part, will be apparent from the description, or may be learned by practice of the presented embodiments.

According to an aspect of an embodiment, there is provided a method of selecting a pathway for a target compound by combining biochemical and chemical processes together, the method including: receiving an input of at least one pathway for synthesis of a target compound or degradation into a target compound; predicting hybrid arrangements of one or more reaction steps included in the at least one pathway; computing a reaction feasibility score for each of the one or more reaction steps of the predicted hybrid arrangements; computing a pathway feasibility score for each of the hybrid arrangements based on the computed reaction feasibility score; sorting the predicted hybrid arrangements based on the computed pathway feasibility score; and selecting at least one of the sorted hybrid arrangements based on the computed pathway feasibility score.

According to an aspect of another embodiment, there is provided a non-transitory computer readable recording medium having recorded thereon a program for performing the method above on a computer.

According to an aspect of another embodiment, there is provided a device for selecting a pathway for a target compound by combining biochemical and chemical processes together, the device including a processor configured to receive input of at least one pathway for synthesis of a target compound or degradation into a target compound, predict hybrid arrangements for one or more reaction steps included in the at least one pathway, compute a reaction feasibility score for each of the one or more reaction steps of the predicted hybrid arrangements, compute a pathway feasibility score for each of the hybrid arrangements based on the computed reaction feasibility score, sort the predicted hybrid arrangements based on the computed pathway feasibility score; and select at least one of the sorted hybrid arrangements based on the computed pathway feasibility score; and a memory coupled to the processor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terms used in the present inventive concept have been selected from currently widely used general terms in consideration of the functions in the present inventive concept. However, the terms may vary according to the intention of one of ordinary skill in the art, case precedents, and the advent of new technologies. Also, for special cases, meanings of the terms selected by the applicant are described below in the description section. Accordingly, the terms used in the present inventive concept are defined based on their meanings in relation to the contents discussed throughout the specification, not by their simple meanings.

In the present specification, when a constituent element "connects" or is "connected" to another constituent element, the constituent element contacts or is connected to the other constituent element not only directly, but also electrically through at least one of other constituent elements interposed therebetween. Also, when a part may "include" a certain constituent element, unless specified otherwise, it may not be construed to exclude another constituent element but may be construed to further include other constituent elements. Terms such as " . . . unit", "~ module", etc. stated in the specification may signify a unit to process at least one function or operation and the unit may be embodied by hardware, software, or a combination of hardware and software.

Terms such as "include" or "comprise" may not be construed to necessarily include any and all constituent elements or steps described in the specification, but may be construed to exclude some of the constituent elements or steps or further include additional constituent elements or steps.

Also, terms such as "first" and "second" are used herein merely to describe a variety of constituent elements, but the constituent elements are not limited by the terms. Such terms are used only for the purpose of distinguishing one constituent element from another constituent element. Hereinafter, the present inventive concept will be described below by explaining preferred embodiments of the inventive concept with reference to the attached drawings.

The present inventive concept relates to a method and a device for selecting an efficient pathway by combining chemical and biochemical processes together for transformation of a target molecule.

Regarding a given transformation nature, a chemical or biochemical approach may be applied based on advantages of each approach to process a target molecule.

Figure 1:
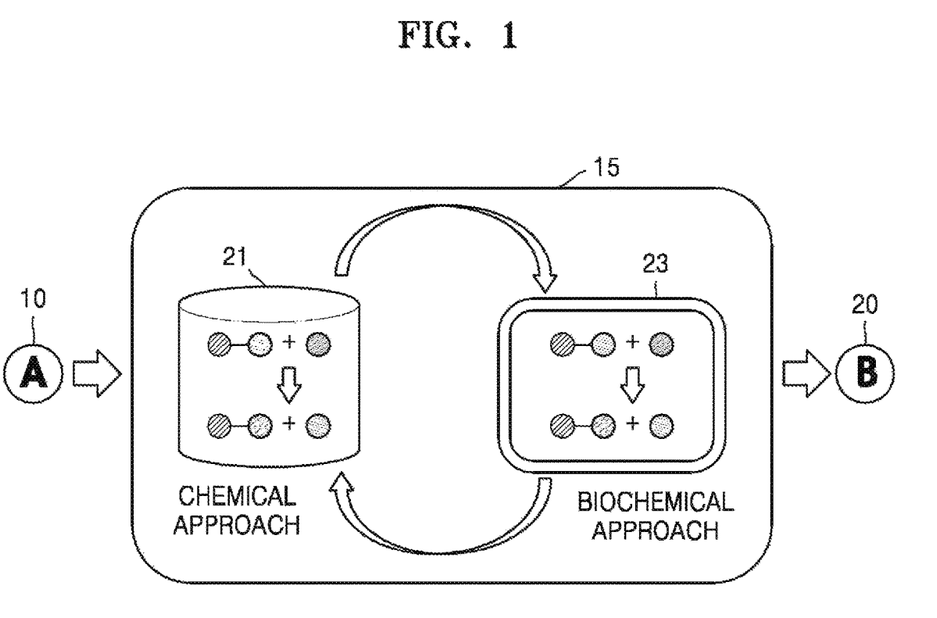
FIG. 1 is a schematic diagram describing a process of transforming Compound A into Compound B, the process being performed by a chemical or biochemical approach, according to an embodiment.

FIG. 1 is a schematic diagram describing a process of transforming Compound A into Compound B, the process being performed by a chemical or biochemical approach, according to an embodiment.

Referring to FIG. 1, a pathway 15 is present to transform a starting compound 10 (i.e., Compound A) into a target compound 20 (i.e., Compound B), and the pathway 15 may include of a variety of reaction steps. In an embodiment, each of the variety of reaction steps of the pathway 15 are predicted to be performed by a chemical approach 21 or a biochemical approach 23, and then, assessed.

Based on the assessment by the chemical approach 21 or the biochemical approach 23, feasible pathways with high efficiency may be predicted. Then, a method of establishing an optimal processing strategy may be provided by selecting one pathway adopting hybrid arrangements where the chemical approach 21 and the biochemical approach 23 are combined together.

That is, in some embodiments, individual reaction steps at a pathway level may be subjected to assessment to thereby select a comparatively efficient approach (e.g., the chemical approach 21 or the biochemical approach 23) for each of the reaction steps.

Figure 2:
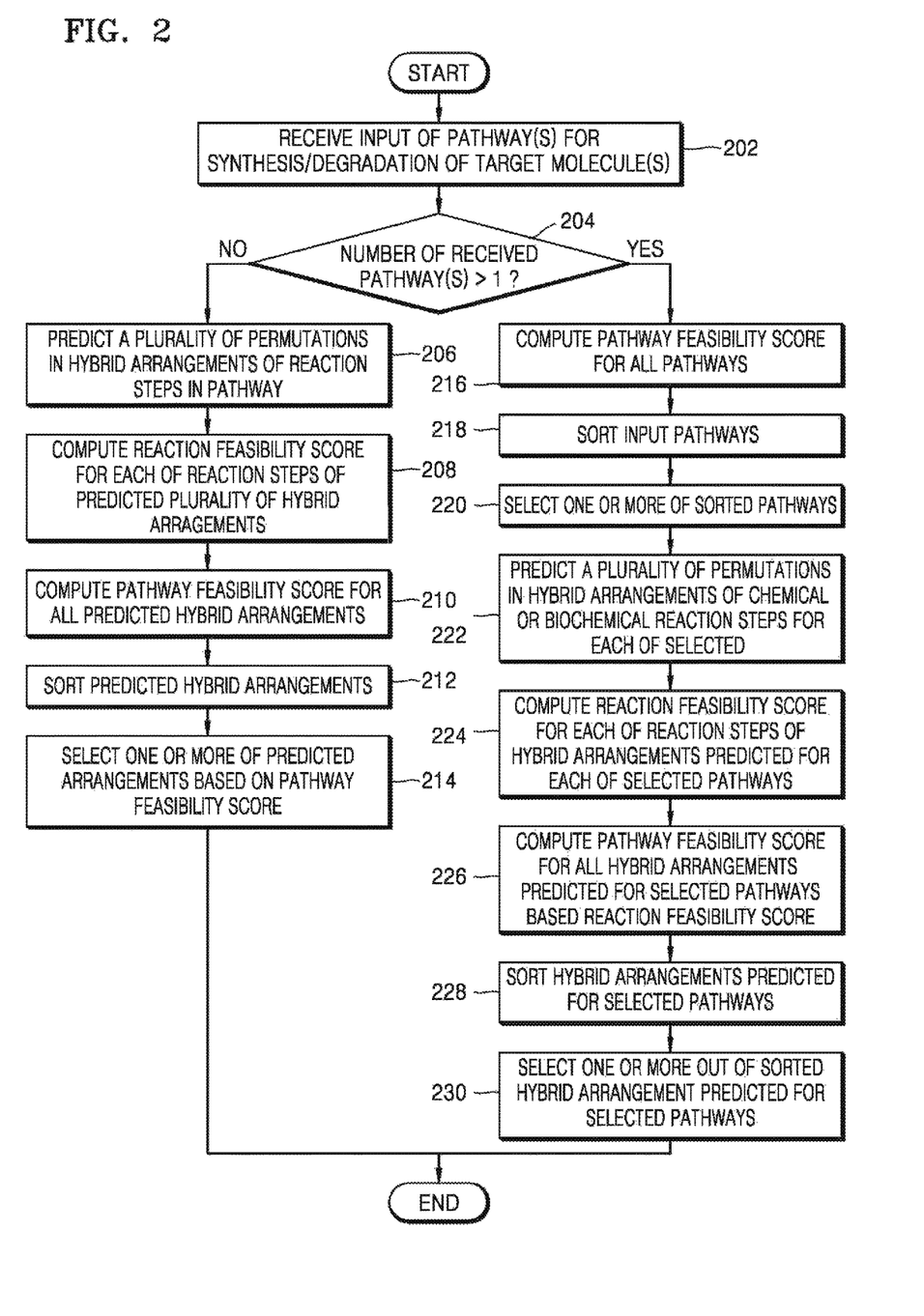
FIG. 2 is a flowchart of a method of selecting a pathway by combining chemical and biochemical processes together to synthesize and degrade a target molecule, according to an embodiment.

FIG. 2 is a flowchart of a method of selecting a pathway by combining chemical and biochemical processes together to synthesize and degrade a target molecule, according to an embodiment.

In operation 202, an input of a pathway for synthesizing or degrading a target molecule is received. The pathway includes a sequential arrangement of reaction steps leading to synthesis or degradation of a target molecule. Synthesis or degradation of a target molecule involves transformation of a starting molecule (also referred to as a starting compound) into a target molecule (also referred to as a target compound). As described above, the reaction steps of the pathway may be either a chemical reaction step performed by a chemical process or a biochemical reaction step performed by a biochemical process.

In operation 204, the number of the received pathway(s) is determined, and more particularly, it is determined whether the number of the received pathway(s) is one or two or more. Then, based on the determined number of the received pathway(s), following steps are selected.

In operation 206, when the number of the received pathway(s) is determined to be one, a plurality of permutations may be predicted with respect to hybrid arrangements of the reaction steps of the received pathway. Each of the reaction steps of the pathway may be a biochemical step performed by a biochemical process or a chemical step performed by a chemical process. For example, when the input pathway has three reactions steps (A→B→C→D), five hybrid arrangements may be present in the three reaction steps.

A knowledgebase, such as a local or remote physical database or databases, may include information about parameters including a biochemical reaction, a chemical reaction, thermodynamic feasibility or kinetic feasibility of the biochemical reaction or chemical reaction, a catalyst for each of the biochemical reaction and the chemical reaction, or yield for each of the biochemical reaction and the chemical reaction. Data included in the knowledgebase may serve as a reference point for analyzing the reaction steps with respect to aforementioned parameters.

In operation 208, a reaction feasibility score is computed for each of the reaction steps of the predicted plurality of hybrid arrangements by referring to the knowledgebase. The reaction feasibility score may be computed based on the following parameters: (a) a yield of reaction steps, (b) a distance between a reference reaction step available in the knowledgebase and the reaction step, and (c) catalyst availability. The parameter of the catalyst availability for the biochemical reaction step refers to availability for an enzyme related to the biochemical reaction step, whereas the catalyst availability for the chemical reaction step refers to availability for a catalyst related to the chemical reaction step.

Furthermore, the availability of the enzyme related to the biochemical reaction step is assessed based on a phylogenetic distance between an organism causing a biochemical reaction to be carried out and a reference organism having a similar or same enzyme. The phylogenetic distance may be calculated as per the methods already known in the art. The availability of the catalyst related to the chemical reaction step is assessed based on a distance between a catalyst and a catalyst most similar to the previous catalyst.

The parameters considered for assessing reaction feasibility are described in Table 1.

TABLE 1

| Parameter | Biochemical reaction | Chemical reaction |
|---|---|---|
| Yield (Y) | Yield from a substrate to a product based on carbon retention, as a post processing for essential reactions | Yield of a particular reaction for a given catalyst and a processing condition |
| Reference reaction distance (S) | Similarity/dissimilarity with respect to the known reactions with similar transformation | Similarity/dissimilarity with respect to the known reactions with similar transformation |
| Catalyst availability score (C) | Availability of an enzyme in an organism or a related organism computed by P | Availability of a catalyst |
| Phylogenetic distance (P) | Phylogenetically distance between the organism undergoing engineering and the source organism reporting the foreign enzyme | N/A |

The reaction feasibility score may be computed by a mathematical function combining independent scores of the parameters of a yield (Y) of reaction steps, a distance (S) between a reference reaction step available in the knowledgebase and a reaction step, and catalyst availability (C) associated with an individual reaction step. In some embodiments, a geometric mean, weighted average, or arithmetic mean of an independent score of the parameters of yield Y, distance S, and catalyst availability (C) may be used, but embodiments are not limited thereto. The feasibility of the reaction steps may be computed and represented by $f_b$ for a biochemical approach or by $f_c$ for a chemical approach.

When the reaction feasibility score is computed for each of the reaction steps, assessment may be performed thereon from the perspective of biochemical and chemical processes. Afterwards, selecting the most feasible option may then be available.

In operation 210, a pathway feasibility score (also referred to as a composite pathway score) may be computed for the predicted hybrid arrangements, based on the computed feasibility score for each of the reaction steps. The pathway feasibility score may be computed as a mathematical function combining the reaction feasibility score for each of the reaction steps forming the predicted hybrid arrangements. The mathematical function may include, for example, a geometric mean, a weighted average, or an arithmetic mean of each of the reaction steps forming the predicted hybrid arrangements, but embodiments are not limited thereto.

The feasibility of each of the predicted hybrid arrangements may be assessed based on the composite pathway score. Here, the higher the score is, the more the feasibility for the particular pathway is, and vice versa.

All possible hybrid arrangements of the received pathways are considered and a design pertaining to the maximum score is considered. A desired objective function for a composite pathway score is defined as follows:

$$\text{Objective function: } \max(P(f_b), P(f_c)). \quad \text{[Equation 1]}$$

In Equation 1, $f_b$ denotes a reaction feasibility score for individual reactions based on a biochemical approach, and $f_c$ denotes a reaction feasibility score for individual reactions based on a chemical approach.

The objective to maximize the power set of reaction feasibilities, i.e., $P(f_b)$ or $P(f_c)$, through the biochemical and chemical approaches may be performed through various methods. In Table 2, two embodiments are summarized.

TABLE 2

| Method | Description | Preference |
|---|---|---|
| Maximum of scores | Consider the maximum of reaction feasibility scores at each reaction step to select an approach | Consider the maximum of reaction feasibility scores at each reaction step to select an approach. |
| Weighted average of individual scores | Consider a weighted average of individual reaction feasibility score for each of the plurality of hybrid arrangements and consider an approach having a maximum value. | Preferable when differences between the reaction feasibility scores by biochemical and chemical approaches are smaller |

Figure 3:
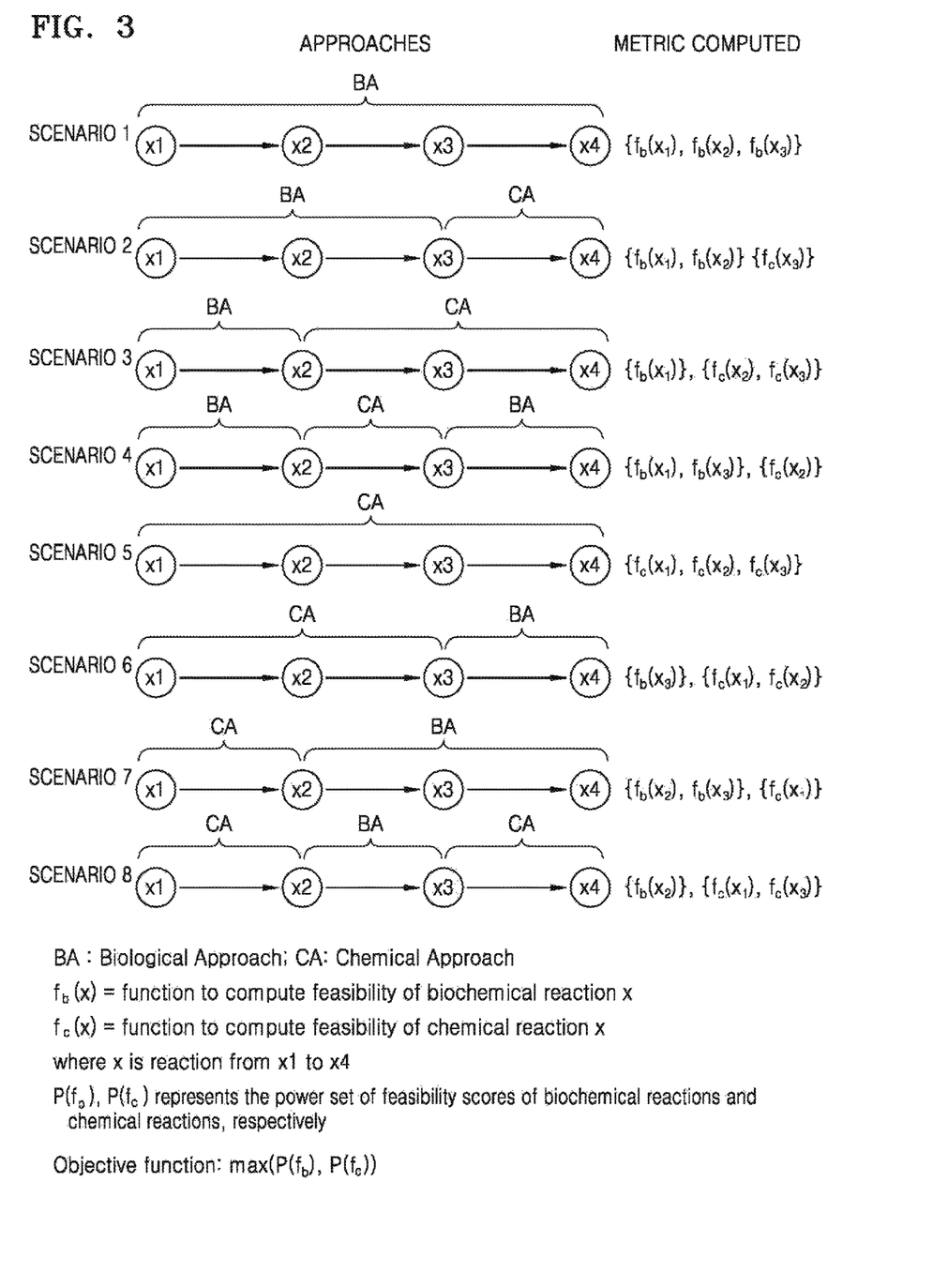
FIG. 3 is a schematic diagram describing evaluation of a processing method performed on Compounds x1 to x4 through a chemical approach or a biochemical (bio-technology) approach, according to an embodiment.

FIG. 3 is a schematic diagram describing evaluation of a processing method performed on Compounds x1 to x4 through a chemical approach or a biochemical (bio-technology) approach, according to an embodiment.

Reaction feasibility may be computed for individual approaches simultaneously through $f_c$ and $f_b$ functions, wherein the power set of $f_c$ and $f_b$ are an objective function to maximize a score.

Referring to FIG. 3, 8 scenarios through which processing can be achieved are illustrated.

Scenario 1 shows processing that can be performed only through a biochemical approach, whereas Scenario 5 shows processing that can be performed only through a chemical approach.

Scenarios 2, 3, 4, 6, 7, and 8 show six hybrid approaches available for processing of Compounds x1 to x4.

Scenario 2 shows a hybrid approach where the first two steps are performed biochemically and the third step is performed chemically.

Scenario 3 shows a hybrid approach where the first step is performed biochemically and the remaining two steps are performed chemically.

Scenario 4 shows a hybrid approach where the first and third steps are performed biochemically and the second step is performed chemically.

Scenario 6 shows a hybrid approach where the first and second steps are performed chemically and the third step is performed biochemically.

Scenario 7 shows a hybrid approach where only the first step is performed chemically and the second and third steps are performed biochemically.

Lastly, scenario 8 shows a hybrid approach where the first and third steps are performed chemically and the second step is performed biochemically.

For each of the scenarios (designs), the composite pathway score is computed based on the feasibility of reactions through functions $f_b$ and $f_c$. The power set is created for the feasibility score of the reactions through a chemical or biochemical approach and for a composite hybrid feasibility score for the hybrid process/scenarios.

Furthermore, in an embodiment, the processing may be optimized by maximization of the computed scores, thereby providing an optimized processing design. A design corresponding to the maximized pathway composite score may be selected as the most optimal chemical processing design.

Referring to FIG. 2 again, in operation 212, the predicted hybrid arrangements are sorted based on the computed pathway feasibility score. The predicted hybrid arrangements may be sorted in an increasing or decreasing order depending on a user's requirement.

In the operation 214, one or more of the hybrid arrangements predicted for the synthesis or degradation of the target molecule may be selected based on the computed pathway feasibility score. For example, a hybrid arrangement having a high pathway feasibility score may be selected.

A hybrid arrangement where a pathway feasibility score is greater than a preset threshold score may be selected. In given scenarios, in the absence of a hybrid arrangement where a pathway feasibility score is greater than a present threshold score, all the hybrid arrangements are discarded. Alternatively, a hybrid arrangement having the same score as the threshold score may be selected as a hybrid arrangement having the highest pathway feasibility score.

Figure 4:
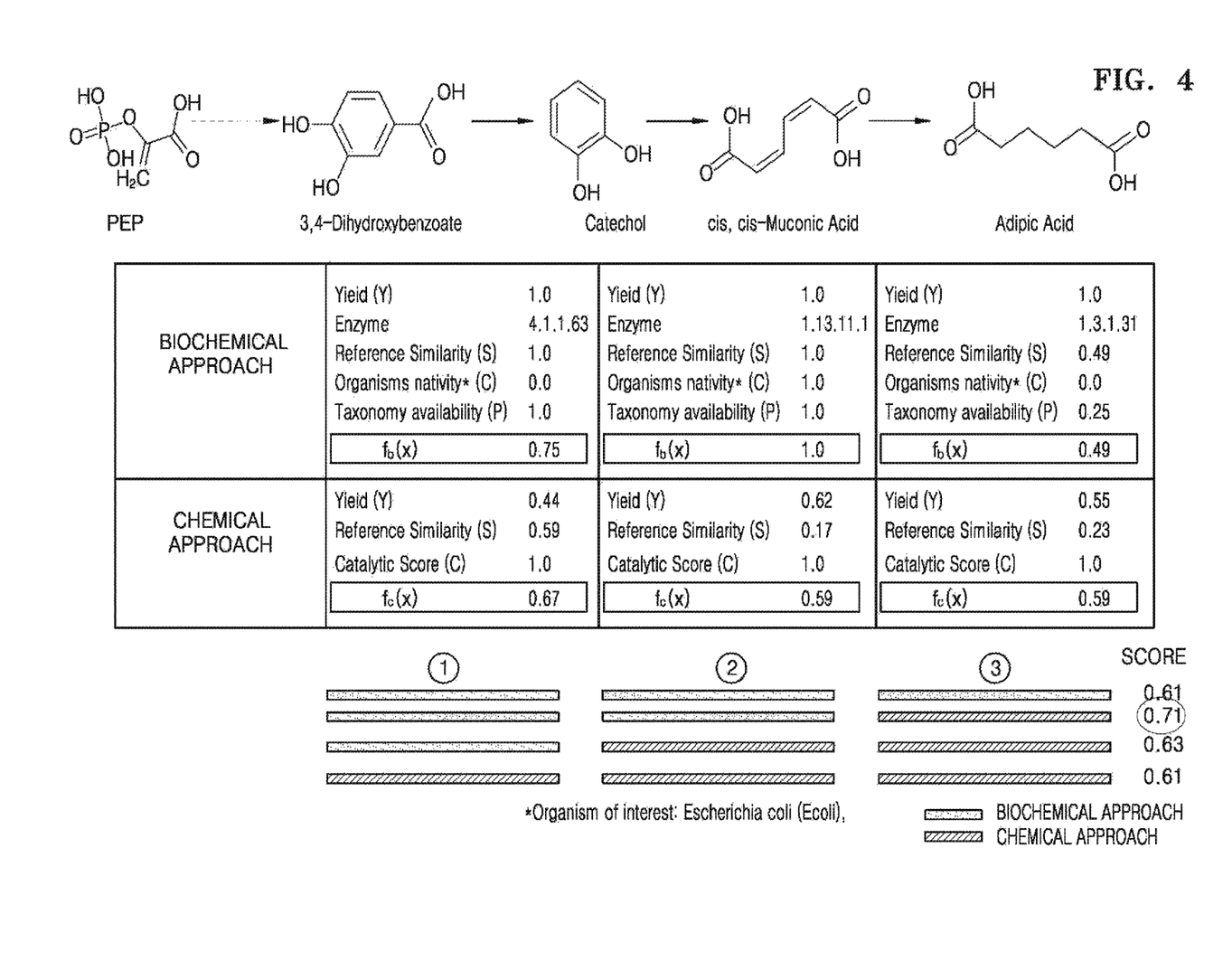
FIG. 4 is a schematic diagram illustrating chemical and biochemical processes for 3-step synthesis of adipic acid from 3,4-dihydroxybenzoate, according to an embodiment.

FIG. 4 is a schematic diagram illustrating chemical and biochemical processes for 3-step synthesis of adipic acid from 3,4-dihydroxybenzoate, according to an embodiment.

Chemical and biochemical feasibilities for individual reaction steps in the pathway are assessed, and the objective function is maximized.

Referring to FIG. 4, the highest pathway feasibility score (0.71) may be obtained for the second hybrid arrangement of the input pathway. Accordingly, based on the scoring scheme computing a reaction feasibility score and a pathway feasibility score, the first two steps may be preferably performed biochemically.

That is, referring to FIG. 4, a step of converting 3,4-dihydroxybenzoate to catechol and a step converting catechol to cis,cis-muconic acid may be preferably performed biochemically. However, the last step of converting cis,cis-muconic acid to adipic acid may be preferably performed chemically.

The pathway for processing phosphoenolpyruvic acid (PEP) to adipic acid as described in FIG. 4 is consistent with the disclosure of US 2009/0305364.

Figure 5:
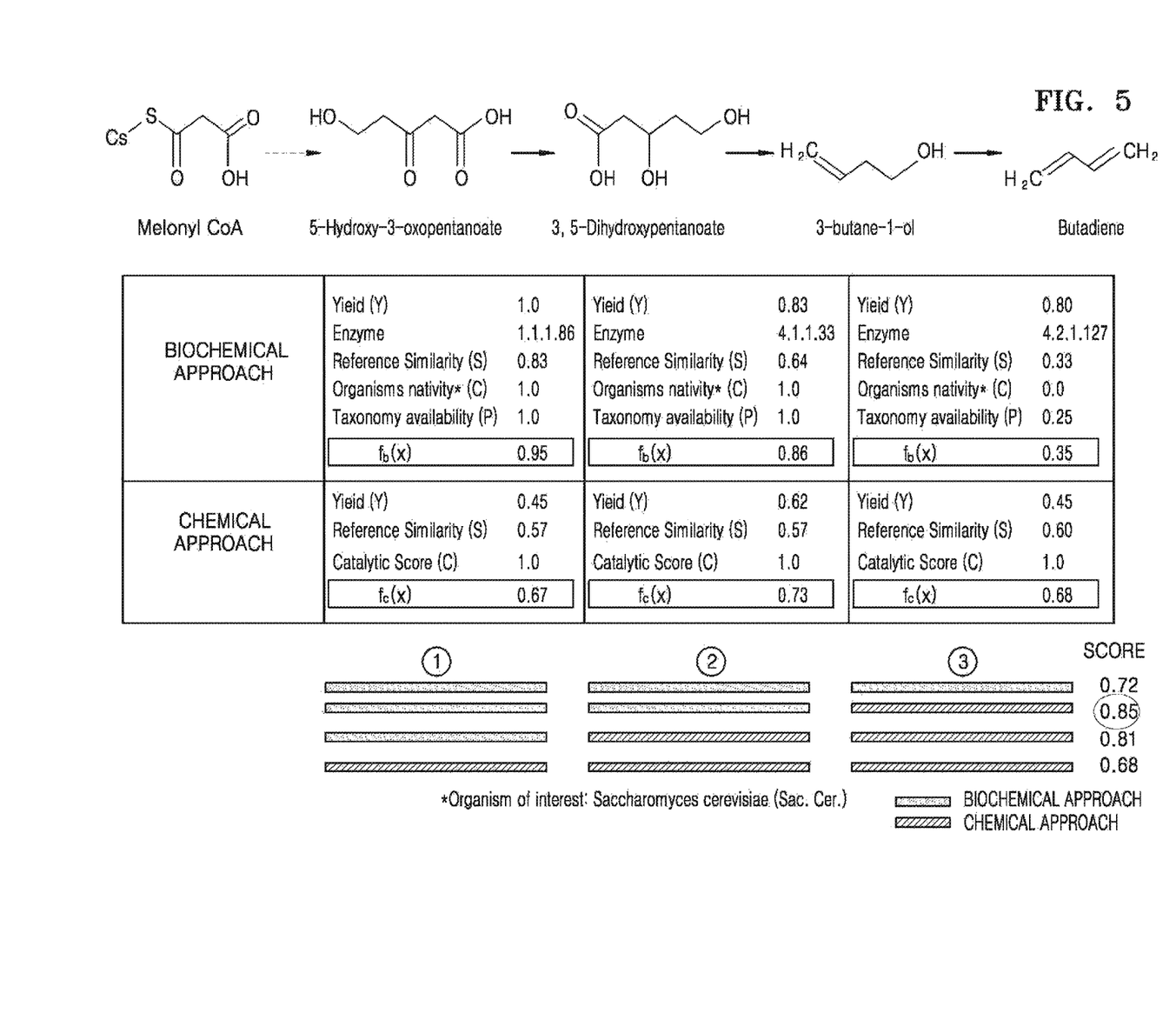
FIG. 5 is a schematic diagram illustrating chemical and biochemical processes for 3-step synthesis of industrially important chemical 1,3 butadiene from 5-hydroxy-3-oxo-pentanoate, according to an embodiment.

FIG. 5 is a schematic diagram illustrating chemical and biochemical processes for 3-step synthesis of industrially important chemical 1,3 butadiene from 5-hydroxy-3-oxopentanoate, according to an embodiment.

Chemical and biochemical feasibilities for individual reactions in the pathway are assessed, and the objective function is maximized.

Referring to FIG. 5, the highest pathway feasibility score (0.85) may be obtained for the second hybrid arrangement of the input pathway. Accordingly, based on the scoring scheme computing a reaction feasibility score and a pathway feasibility score, the first step of converting 5-hydroxy-3-oxopentanoate to 3,5-dihydroxypentanoate may be preferably performed biochemically. In addition, the second step of converting 3,5-dihydroxypentanoate to 3-butane-1-ol may be preferably performed biochemically. However, the last step of converting 3-butane-1-ol to 1,3 butadiene may be preferably performed chemically.

The pathway for processing 5-hydroxy-3-oxopentanoate to 1,3 butadiene as described in FIG. 5 is consistent with the disclosure of US 2012/0021478.

In another embodiment, the method of selecting a pathway by combining chemical and biochemical processes together may additionally include a step of imposing a penalty for each approach transition by reducing the pathway feasibility score of individual hybrid arrangements in a manner associated with a predetermined number.

As known in the art, the biochemical and chemical processes may occur entirely in different environments/set ups. Therefore, during the performance of the reaction steps, switching of one type of a process to another type of a process may be easily done. Every approach transition in the pathway processing may add a certain level of discomfort to a user. The concept using a penalty may be introduced to balance out the discomfort added by each or every approach transition in the hybrid pathway.

In some embodiments associated with the imposing of the penalty, the penalty may be imposed for every approach transition from one type of a process to another type of a process in the sequential arrangement of the reaction steps.

In some embodiments associated with the imposing of the penalty, the penalty may be imposed after the first approach transition at the very beginning.

In some embodiments associated with the imposing of the penalty, the penalty may be imposed may be imposed in a way that the penalty gradually increases from a lower number to a higher number as the number of the approach transitions increases.

In some embodiments, the method of selecting a pathway by combining chemical and biochemical processes may further include a step of ranking the selected hybrid arrangement of the received pathway based on a preset criterion. The preset criterion for ranking may include, for example, a pathway feasibility score that is greater than a given threshold value.

Regarding the scenarios where the number of pathways determined in the operation 204 is more than one, other operations may be performed instead of the operation 206. In the first embodiment, all the received pathways are not processed, but a screening stage may be performed first to find a final candidate only for the efficient pathway. In the second embodiment, all the received processes are processed.

In the first embodiment associated with the screening stage, only few (one or more) of the received pathways are selected to be further processes, and the remaining pathways are discarded. When the number of the input pathways is more than one in operation 216, the pathway feasibility for each of the input pathway is computed. At this stage, the pathway feasibility scores (the composite pathway scores) for all the received pathways are computed in a similar manner as described in connection with the operation 210.

In operation 218, the pathways are sorted based on the pathway feasibility scores thereof. The sorting process at this state is performed in a similar manner as described in connection with the operation 212.

In operation 220, one or more of the sorted pathways are selected based on the pathway feasibility scores thereof. The selection process at this stage is performed in a similar manner as described in connection with the operation 214.

In operation 222, a plurality of permutations in hybrid arrangements of the chemical or biochemical reaction steps are predicted for each of the selected pathways. The prediction for each of the selected pathways is performed in a similar manner as described in connection with the operation 206.

In operation 224, the reaction feasibility score is computed for each of the reaction steps of the hybrid arrangements predicted for each of the selected pathways. The reaction feasibility score is computed in a similar manner as described in connection with the operation 208.

In operation 226, the pathway feasibility score (the composite pathway score) is computed for all the hybrid arrangements predicted for the selected pathways based on the reaction feasibility score. The pathway feasibility score is computed in a similar manner as described in connection with the operation 210.

In operation 228, the hybrid arrangements predicted for the selected pathways are sorted based on the pathway feasibility score. The sorting is performed in a similar manner as described in connection with the operation 212.

In operation 230, one or more out of the sorted hybrid arrangement predicted for the selected pathways are selected based on a user's requirement.

Furthermore, when the number of the received pathways is more than one, in some embodiments, the method for selecting a pathway may be modified to include chemical or biochemical analysis of the received pathways before computing the pathway feasibility score for the input pathways as a part of the screening stage. That is, after the operation 204, the input of the pathways may be processed so as to (a) identify a biochemical and chemical phenomenon of the pathways, (b) identify similarity in the reaction steps of the pathways, or (c) identify similarity of the target molecules on which the pathways are performed.

Based on the processing described above, there may be two scenarios. According to scenario (a), the input pathways have different reaction steps from each other and are treated by one of biochemical and chemical processes, thereby producing similar target molecules. According to scenario (b), the input pathways have different reaction steps from each other and are treated by a combination of biochemical and chemical processes, thereby producing similar target molecules.

Such processing may be followed by the screening step as described in the operation 216.

Furthermore, operations 222 to 230 may be performed as described above.

Figure 6:
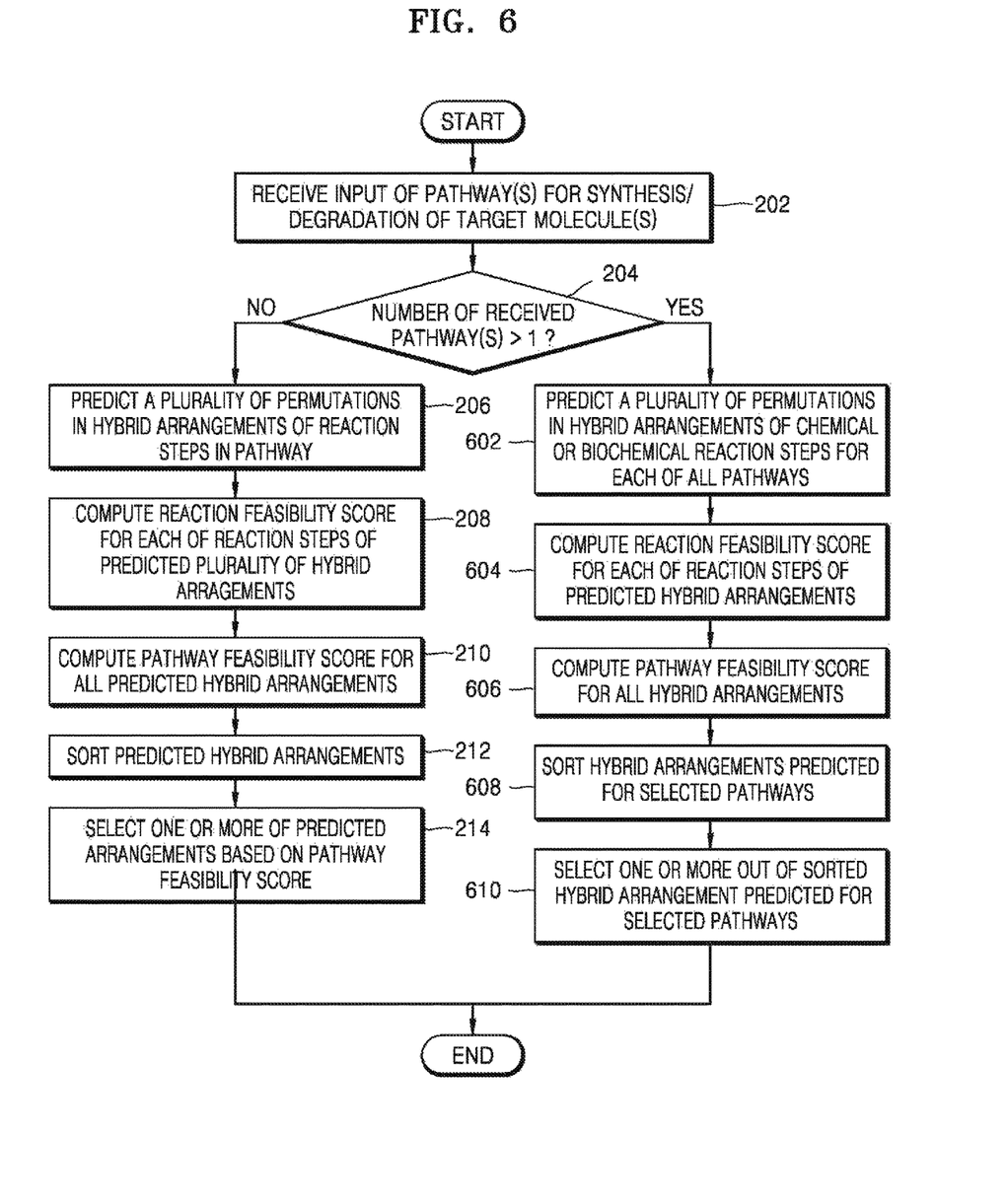
FIG. 6 is a flowchart describing that all the received pathways are processed without any discrimination, according to an embodiment.

FIG. 6 is a schematic diagram describing that all the received pathways are processed without any discrimination, according to an embodiment.

In operation 602, a plurality of permutations in hybrid arrangement are predicted for the reaction steps of the received input pathways. The prediction of the permutations is performed in a similar manner as described in connection with the operation 206.

In operation 604, the reaction feasibility score is computed for each of the reaction steps of the hybrid arrangements predicted for each of the received pathways. The reaction feasibility score is computed in a similar manner as described in connection with the operation 208.

In operation 606, the pathway feasibility score (the composite pathway score) is computed for all the hybrid arrangements predicted for each of the received pathways based on the reaction feasibility score. The pathway feasibility score is computed in a similar manner as described in connection with the operation 210.

In operation 608, the hybrid arrangements predicted for all received pathways are sorted based on the pathway feasibility score thereof. The sorting is performed in a similar manner as described in connection with the operation 212.

In operation 610, one or more out of the sorted hybrid arrangements predicted for all the received pathways are selected.

Figure 7:
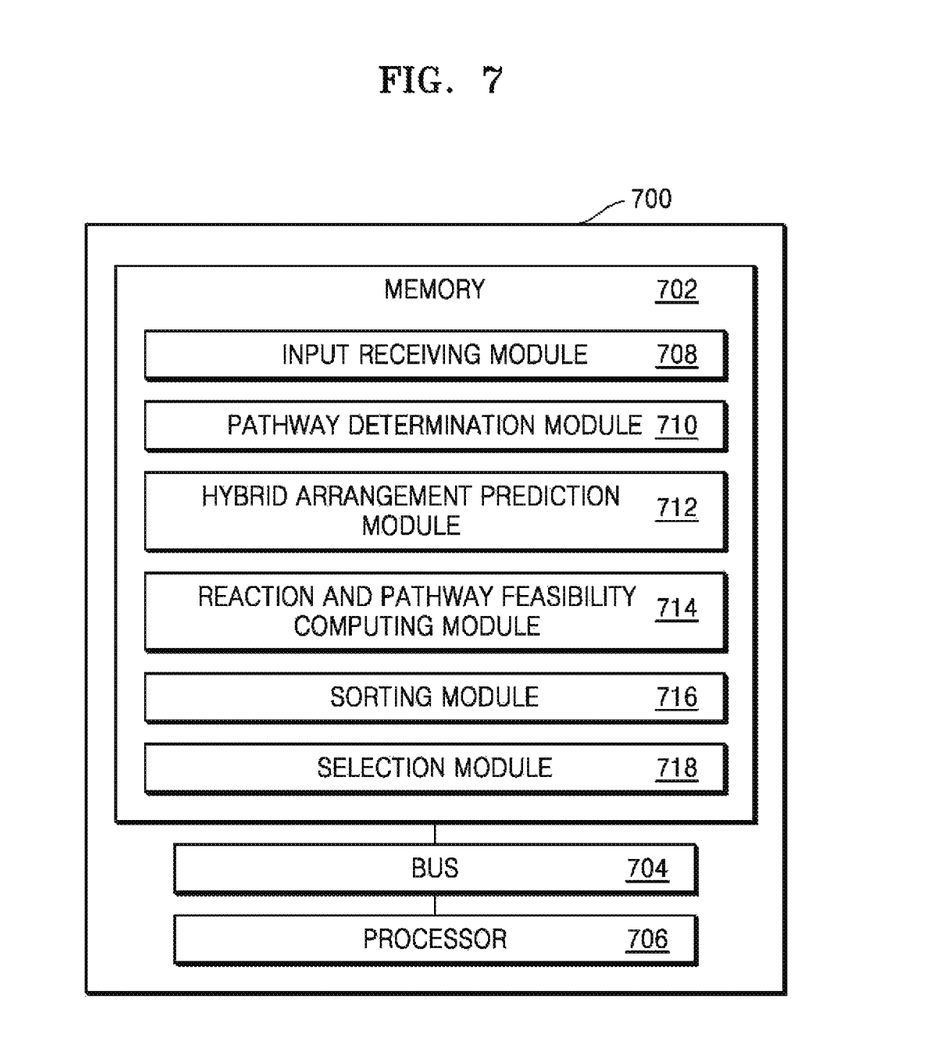
FIG. 7 is a block diagram of a device for selecting a pathway by combining chemical and biochemical processes together in terms of synthesis and degradation of a target molecule, according to an embodiment.

FIG. 7 is a block diagram of a device 700 for selecting a pathway by combining chemical and biochemical processes together in terms of synthesis and degradation of the target molecule, according to an embodiment.

The device 700 includes a processor 706 and a memory 702 coupled to the processor 706.

The processor 706 may be implemented by any type of a computational circuit, and for example, may be a microprocessor, a microcontroller, a complex instruction set computing (CISC) microprocessor, a reduced instruction set computing (RISC) microprocessor, a very long instruction word (VLIW) microprocessor, an explicitly parallel instruction computing (EPIC) microprocessor, a digital signal processor (DSP), or any other type of the processing circuit, or a combination thereof.

The memory 702 includes a plurality of modules stored in the form of an executable program which instructs the processor 706 to perform all the operations illustrated in FIGS. 2 and 6. The memory 702 may include an input receiving module 708, a number of pathway determination module 710, a hybrid arrangement prediction module 712, a reaction and pathway feasibility computing module 714, a sorting module 716, and a selection module 718.

Computer memory elements may include any suitable memory device for storing data and an executable program, such as read only memory (ROM), random access memory (RAM), erasable programmable read only memory (EPROM), electrically erasable programmable read only memory (EEPROM), hard drive, removable media drive for handling memory cards and the like. In some embodiments, the computer memory elements may be implemented in conjunction with program modules, implemented so as to include functions, procedures, data structures, and application programs, implemented so as to perform tasks, or implemented so as to define an abstract data type (ADT) or low-level hardware contexts. An executable program stored on any of the above-mentioned storage media may be executable by the processor 706.

The input receiving module 708 instructs the processor 706 to perform the operation 202 of FIG. 2 or 6.

The number of pathway determination module 710 instructs the processor 706 to perform the operation 204 of FIG. 2 or 6.

The hybrid arrangement prediction module 712 instructs the processor 706 to perform the operations 206 and 222 of FIG. 2.

In some embodiments, the hybrid arrangement prediction module 712 instructs the processor 706 to perform the operations 206 and 602 of FIG. 6.

The reaction and pathway feasibility computing module 714 instructs the processor 706 to perform the operations 208, 210, 216, 224, and 226 of FIG. 2.

In some embodiments, the reaction and pathway feasibility computing module 714 instructs the processor 706 to perform the operations 208, 210, 604, and 606 of FIG. 6.

The sorting module 716 instructs the processor 706 to perform the operations 212 and 218 of FIG. 2.

In some embodiments, the sorting module 716 instructs the processor 706 to perform the operations 212 and 608 of FIG. 6.

The selection module 718 instructs the processor 706 to perform the operations 214, 220, and 230 of FIG. 2.

In some embodiments, the selection module 718 instructs the processor 706 to perform the operations 214 and 610 of FIG. 6.

Figure 8:
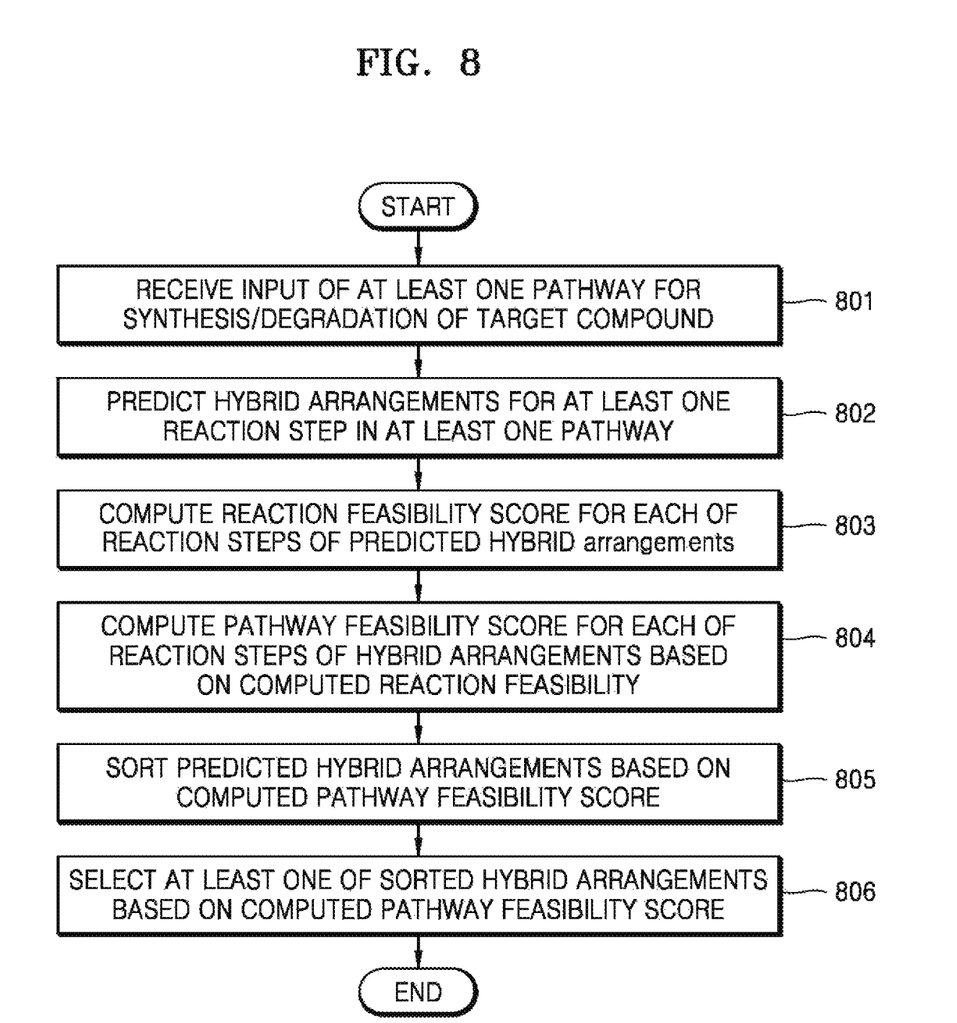
FIG. 8 is a flowchart of a method of selecting a pathway by combining chemical and biochemical processes together in terms of synthesis and degradation of a target molecule, according to an embodiment.

FIG. 8 is a flowchart of the method of selecting a pathway by combining chemical and biochemical processes together in terms of synthesis and degradation of a target molecule, according to an embodiment.

In operation 801, the processor 706 receives input of at least one pathway for synthesis of a target compound or degradation into a target compound. Here, the pathway may include sequential arrangement of one or more reaction steps, wherein each of the one or more reaction steps may include at least one of a chemical reaction step performed by a chemical process and a biochemical reaction step performed by a biochemical process.

In operation 802, the processor 706 predicts hybrid arrangements for at least one reaction step of the at least one pathway.

In operation 803, the processor 706 computes a reaction feasibility score for each of the reaction steps in the predicted hybrid arrangements. The reaction feasibility score is computed based on at least one of parameters of a yield of reaction steps, a distance between a reference reaction step available in the knowledgebase and the reaction step, and catalyst availability. The parameter of the catalyst availability for the biochemical reaction step refers to availability for an enzyme related to the biochemical reaction step, whereas the catalyst availability for the chemical reaction step refers to availability for a catalyst related to the chemical reaction step.

In operation 804, the processor 706 computes a pathway feasibility score for each of the reaction steps of the hybrid arrangements, based on the computed feasibility score. The pathway feasibility score is computed by a mathematical function combining the reaction feasibility scores computed for each of the reaction steps.

In operation 805, the processor 706 sorts the predicted hybrid arrangements, based on the computed pathway feasibility score.

In operation 806, the processor 706 selects at least one of the sorted hybrid arrangements, based on the computed pathway feasibility score. Here, the processor 706 may select a hybrid arrangement where a pathway feasibility score is greater than a preset threshold score.

The embodiments of the present inventive concept may include a processor, a memory for storing and executing program data, a permanent storage such as a disk drive, a communication port for communication with an external device, and a user interface device including a touch panel, a key, and a button. Methods implemented by software modules or algorithms may be stored in a non-transitory computer-readable recording medium in the form of a computer-readable code or a program order that is executable by the processor. Here, the non-transitory computer-readable recording medium may include a magnetic storage medium (e.g., ROM, RAM, a floppy disk, a hard disk, and the like) or an optical readable medium (e.g., a CD-ROM, a digital versatile disc (DVD), and the like). The non-transitory computer-readable recording medium is distributed to computer systems connected to a network, and accordingly, computer-readable codes may be stored and executed according to a distribution method. A medium can be readable by a computer, stored by a memory, and include programs executed by a processor.

The present embodiments can be represented by functional block configurations and various processing operations. Such functional blocks can be implemented by the various numbers of hardware and/or software that executes particular functions. For example, the direct circuit configuration, such as a memory, a processing, a logic, or a look-up table that can execute various functions by controlling at least one microprocessor or using a different controlling device, can be described in the embodiments. Similarly to the components that can be executed in software programming or as software elements, various algorithms that are implemented by data structures, processes, routines, or a combination of other programming components are described in the present embodiments, and accordingly, such algorithms can be implemented by programming or scripting languages, such as C, C++, Java, or assembler. Functional aspects of the present inventive concept can be implemented with an algorithm that is executable on at least one processor. In addition, techniques in the related art for electronic settings, signal processing, and/or data processing can be described in the present embodiments. The terms "mechanism," "element," "means," and "configuration" can be widely used, and are not limited to mechanical and physical configurations. These terms can be linked to processors or the like, thereby including the meaning of a series software routines.

The specific aspects described in the present embodiments are for exemplification purposes only, and are not intended to limit technical scope of any embodiment. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the operations of all methods described herein can be performed in any suitable order unless otherwise indicated herein or otherwise clearly contradicted by context. The inventive concept is not limited to the described order of the operations.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of selecting a pathway for a target compound by combining biochemical processes and chemical processes together, comprising the steps, implemented in silico in a processor, of:
   receiving an input of at least one pathway having a plurality of reaction steps for synthesis of the target compound or degradation into the target compound;
   receiving, from a knowledgebase, parameters relating to: at least one biochemical reaction, and at least one chemical reaction, of the plurality of reaction steps;
   predicting hybrid arrangements of one or more reaction steps included in the at least one pathway;
   computing a reaction feasibility score for each of the one or more reaction steps of the predicted hybrid arrangements based on the parameters received from the knowledgebase;
   computing a pathway feasibility score for each of the hybrid arrangements based on the computed reaction feasibility score;
   sorting the predicted hybrid arrangements based on the computed pathway feasibility score; and
   selecting at least one of the sorted hybrid arrangements based on the computed pathway feasibility score.

2. The method of claim 1, wherein each of the one or more reaction steps comprises at least one of a chemical reaction step performed by a chemical process and a biochemical reaction step performed by a biochemical process, and
   the pathway comprises a sequential arrangement of the one or more reaction steps.

3. The method of claim 1, wherein the parameters further include at least one of: a yield of a reaction step, a distance between a reference reaction step available in the knowledgebase and the reaction step, and catalyst availability.

4. The method of claim 3, wherein the reaction feasibility score is computed based on the catalyst availability.

5. The method of claim 1, wherein the pathway feasibility score is computed by a mathematical function combining the reaction feasibility scores computed for each of the one or more reaction steps.

6. The method of claim 1, wherein the selecting of the at least one of the sorted hybrid arrangements further comprises:
   selecting at least one hybrid arrangement where the computed pathway feasibility score is greater than a preset threshold score.

7. The method of claim 1, wherein the method further comprises determining a number of the at least one pathway received through the input,
   wherein, when the number of the at least one pathway is determined to be two or more, the predicting of the hybrid arrangements predicts a plurality of permutations with respect to the hybrid arrangements of the one or more reaction steps included in each of the two or more pathways.

8. The method of claim 7, wherein, when the number of the at least one pathway is determined to be one, the predicting of the hybrid arrangements predicts a plurality of permutations with respect to the hybrid arrangements of the one or more reaction steps in the one pathway.

9. The method of claim 7, wherein the predicting of the hybrid arrangements of the one or more reaction steps in each of the two or more pathways further comprises:
   computing a pathway feasibility score for each of the two or more pathways;
   sorting the pathways based on the computed pathway feasibility scores; and
   selecting at least one pathway from the sorted pathways where the computed pathway feasibility score is greater than a preset threshold score.

10. A non-transitory computer readable recording medium containing a program for performing on a computer an in silico method comprising:
    receiving an input of at least one pathway having a plurality of reaction steps for synthesis of a target compound or degradation into the target compound;
    receiving, from a knowledgebase, parameters relating to: at least one biochemical reaction, and at least one chemical reaction, of the plurality of reaction steps;
    predicting hybrid arrangements of one or more reaction steps included in the at least one pathway;
    computing a reaction feasibility score for each of the one or more reaction steps of the predicted hybrid arrangements based on the parameters received from the knowledgebase;
    computing a pathway feasibility score for each of the hybrid arrangements based on the computed reaction feasibility score;
    sorting the predicted hybrid arrangements based on the computed pathway feasibility score; and
    selecting at least one of the sorted hybrid arrangements based on the computed pathway feasibility score.

11. A device for selecting, in silico, a pathway for a target compound by combining biochemical and chemical processes together, the device comprising:
    a processor and a memory coupled to the processor, the memory containing code, which when executed by the processor causes the processor to:
    receive input of at least one pathway having a plurality of reaction steps for synthesis of the target compound or degradation into the target compound,
    receive, from a knowledgebase, parameters relating to: at least one biochemical reaction, and at least one chemical reaction, of the plurality of reaction steps,
    predict hybrid arrangements for one or more reaction steps included in the at least one pathway,
    compute a reaction feasibility score for each of the one or more reaction steps of the predicted hybrid arrangements based on the parameters received from the knowledgebase,
    compute a pathway feasibility score for each of the hybrid arrangements based on the computed reaction feasibility score,
    sort the predicted hybrid arrangements based on the computed pathway feasibility score; and
    select at least one of the sorted hybrid arrangements based on the computed pathway feasibility score.

12. The device of claim 11, wherein each of the one or more reaction steps comprises at least one of a chemical reaction step performed by a chemical process and a biochemical reaction step performed by a biochemical process, and
    the pathway comprises a sequential arrangement of the one or more reaction steps.

13. The device of claim 11, wherein the parameters further include at least one of: a yield of a reaction step, a distance between a reference reaction step available in the knowledgebase and the reaction step, and catalyst availability.

14. The device of claim 13, wherein the reaction step reaction feasibility score is computed based on the catalyst availability.

15. The device of claim 11, wherein the pathway feasibility score is computed by a mathematical function combining reaction feasibility scores computed for each of the one or more reaction steps.

16. The device of claim 11, wherein the code further comprises code to select a hybrid arrangement where the computed pathway feasibility score is greater than a preset threshold score.

17. The device of claim 11, wherein the code further comprises code to:
   determine a number of at least one pathway received through the input, and
   wherein, when the number of the at least one pathway is determined to be two or more, the processor is further caused to predict a plurality of permutations with respect to the hybrid arrangements of the one or more reaction steps included in each of the two or more pathways.

18. The device of claim 17, wherein, when the number of the at least one pathway is determined to be one, the processor is further configured to predict a plurality of permutations with respect to the hybrid arrangements of the one or more reaction steps in the one pathway.

19. The device of claim 17, wherein, when the number of the at least one pathway is determined to be two or more, the code further comprises code to:
   compute a pathway feasibility score for each of the two or more pathways,
   sort the pathways based on the computed pathway feasibility scores, and
   select at least one pathway from the sorted pathways where the computed pathway feasibility score is greater than a preset threshold score.

20. The method of claim 1, wherein selecting at least one of the sorted hybrid arrangements based on the computed pathway feasibility score comprises:
   selecting the biochemical reaction or the chemical reaction for the each of the one or more reaction steps of the predicted hybrid arrangements;
   maximizing an objective function of biochemical and chemical reaction feasibility scores for a composite pathway score; and
   selecting a designed pathway for the target compound having the maximized objective function for the composite pathway score.

* * * * *